United States Patent [19]

Pratt, Jr.

[11] Patent Number: 5,258,622

[45] Date of Patent: Nov. 2, 1993

[54] APPARATUS AND METHOD FOR MEASURING PHYSICAL CHARACTERISTICS OF MATERIALS

[75] Inventor: James D. Pratt, Jr., Raleigh, N.C.

[73] Assignee: Troxler Electronic Laboratories, Inc., Research Triangle Park, N.C.

[21] Appl. No.: 850,554

[22] Filed: Mar. 13, 1992

[51] Int. Cl.$^5$ ............................................. G01N 23/00
[52] U.S. Cl. ............................ 250/390.05; 250/390.04; 250/358.1
[58] Field of Search ............. 250/358.1, 360.1, 390.04, 250/390.05, 390.06, 506.1, 252.1 R, 253, 255

[56] References Cited

U.S. PATENT DOCUMENTS

| | | |
|---|---|---|
| 3,626,183 | 12/1971 | Berry et al. |
| 3,911,271 | 10/1975 | Mitchell |
| 4,039,809 | 8/1977 | Bailey |
| 4,196,614 | 4/1980 | McLaughlin |
| 4,243,886 | 1/1981 | Untermyer, II |
| 4,381,452 | 4/1983 | Jeunehomme |
| 4,439,675 | 3/1984 | Campbell ............... 250/358.1 X |
| 4,524,279 | 6/1985 | Christianson et al. ....... 250/252.1 X |
| 4,615,215 | 10/1986 | Sugimoto et al. |
| 4,686,852 | 8/1987 | Ito et al. |

FOREIGN PATENT DOCUMENTS

| | | | |
|---|---|---|---|
| 41-200 | 1/1966 | Japan | 250/390.05 |
| 714895 | 2/1991 | U.S.S.R. | 250/390.05 |
| 1213961 | 11/1970 | United Kingdom | |

OTHER PUBLICATIONS

Mitchell, Terry M., "Measurement of Cement Content by Using Nuclear Backscatter-and-Absorption Gauge"; Transportation Research Board Record 692 (1978), pp. 34-40.

Iddings, Frank A., and Arman, Ara, "Determination of Cement Content in Soil Cement Mixtures and Concrete"; Engineering Research Bulletin No. 114, Division of Engineering Research, Louisiana State University, Apr., 1977.

Iddings, Frank A. et al., "Nuclear Techniques for Cement Determination"; Nat Acad Sciences—Nat Research Council—Highway Research Rec, n. 268, 1969, pp. 118-130.

Mitchell, T. M., "Nuclear Cement Content Gage—Instruction Manual"; U.S. Department of Transportation Report No. FHWA-RD-75-63, May 1975.

Gulden W., "Nuclear Cement Content Gage—Performance Evaluation"; Georgia Dept. of Transportation, Report No. FHWA-RD-75-525, May 1975.

Tom, J. G. and Magoun, A. D., "Evaluation of Procedures Used To Measure Cement And Water Content In Fresh Concrete"; National Cooperative Highway Research Program Report 284, Jun. 1986.

Shah, S. C. and Melancon, J. L., "Nuclear Cement Content Gage—Comparison Analysis"; Louisiana Dept. of Transportation and Development, Report No. FHWA-TS-78-201; Aug. 1977.

(List continued on next page.)

Primary Examiner—Constantine Hannaher
Assistant Examiner—Edward J. Glick
Attorney, Agent, or Firm—Bell, Seltzer, Park & Gibson

[57] ABSTRACT

An instrument and a method are provided for determining the moisture and cement contents of fresh concrete and for calculating and displaying to the user of the instrument the projected strength of the concrete. The instrument has two probes, each probe containing a low-activity nuclear source. The probes are stored in shielded receptacles in a housing when not in use. The user calibrates the probes with reference to concrete compositions of known cement and water content, and then for field use separately inserts each probe into the access tube of a sample pan filled with concrete to obtain counts corresponding to moisture content and cement content. An electronics unit is attached to the housing for storing the correlations and performing the calculations.

35 Claims, 6 Drawing Sheets

OTHER PUBLICATIONS

Hime, W. G. and Willis, R. A., "A Method for the Determination of the Cement Content of Plastic Concrete"; Research Department Bulletin 61: Authorized Reprint from the Copyrighted ASTM Bulletin No. 209, Oct. 1955.

Naik, Tarun R. and Ramme, Bruce W., "Determination of the Water Content of Concrete By the Microwave Method"; Cement and Concrete Research, vol. 17, pp. 927-938, 1987.

Kelly, R. T. and Vail, J. W., "Rapid Analysis of Fresh Concrete"; Concrete, Apr. 1968.

Dhir, Ravindra K. et al., "Analysis of fresh concrete: determination of cement content by the Rapid Analysis Machine"; Magazine of Concrete Research: vol. 34, No. 119: Jun. 1982.

Mitchell, T. M., "A Radioisotope Backscatter Gauge For Measuring The Cement Content of Plastic Concrete"; U.S. Department of Transportation, Report No. FHWA-RD-73-48, Apr. 1973 Interim Report.

Industry Report, "Density Gauge Hastens Analysis", Electronics, Oct. 1, 1957, p. 24.

Lepper, Jr. et al., "Nuclear Methods for Determining the Water Content and Unit Weight of Fresh Concrete", Journal of Materials, vol. 6, No. 4, 1971, pp. 826-841.

APPARATUS AND METHOD FOR MEASURING PHYSICAL CHARACTERISTICS OF MATERIALS

FIELD OF THE INVENTION

This invention relates to an apparatus and a method for measuring the physical characteristics of materials.

BACKGROUND OF THE INVENTION

One problem facing the construction industry is controlling the quality or strength of concrete in structures such as buildings and roadways. Fresh concrete requires about twenty eight days to cure to its full strength, and so compressive strength tests can be performed on fully set concrete only after a significant delay between pouring of the fresh concrete and curing. Accelerated curing techniques have been employed to shorten the time, but any method that determines the strength of concrete after it has been poured into a structure at a construction site generally is considered too late.

A correlation between the water to cement ratio of fresh, unhardened concrete and the ultimate strength of a fully cured concrete has been used to predict the ultimate attainable strength of fresh concrete. In connection therewith, several methods have been proposed and there are some ASTM standards for separately measuring the water and cement contents of fresh concrete mix. Most of these methods generally rely upon laboratory procedures such as mechanical separation and weighing of the concrete components, which are time consuming and involved and are not suitable for fast, on-site determination of concrete quality. Examples of these methods are contained in U.S. Pat. Nos. 4,196,614 and 4,615,215.

Various nuclear apparatus and methods have also been proposed for separately determining either the water content or the cement content of a fresh concrete mix, but problems have been encountered. U.S. Pat. No. 3,911,271 to Mitchell relates to one such portable nuclear device for determining the cement content of fresh concrete, but the device apparently never was commercialized. The Mitchell nuclear cement content gauge used a sodium iodide scintillation crystal and was subject to electronic drift over time and in response to temperature changes. The Mitchell nuclear cement content gauge has been extensively reported on by the Federal Highway Administration in its report Nos. FHWA-RD-73-48, FHWA-RD-75-63, FHWA-RD-75-525, and FHWA-TS-78-201. See also report No. 284 of the National Cooperative Highway Research Program, which was published in June, 1986.

With the foregoing problems in mind, it is an object of the present invention to overcome the limitations of the prior apparatus and methods discussed above and to provide an apparatus and method for quickly and easily determining the physical properties of materials. A more specific object of the invention is to provide an apparatus and method that is suitable for field use in determining the moisture and cement content of fresh, unhardened concrete. A still more specific object of the invention is to provide an apparatus and method that is suitable for field use in determining the ultimate attainable strength of a fresh concrete mix.

SUMMARY OF THE INVENTION

In accordance with the present invention, a portable, self-contained instrument is provided for measuring the physical properties of test materials and for displaying to the user of the instrument a value for at least one physical characteristic of the test material. The instrument includes a housing to which is connected a pair of movable probes that are adapted to be individually positioned in measuring contact with a sample of the test material. The first movable probe of the pair includes a means for obtaining a measurement of a first physical property of the test material and the second movable probe of the pair includes a means for obtaining a measurement of a different physical property of the test material. An electronic circuit is operatively connected to each of the probes and includes a means for receiving signals from each of the probes that indicate the properties the probes are measuring. The electronic circuit also includes a means for determining from these signals a value for at least one physical characteristic of the test material. The display device is operatively connected to the electronic circuit so that the value of the physical characteristic of the test material will be displayed to the user of the instrument.

More specifically, the first and second probes comprise low activity radiation sources and radiation detectors. The instrument housing includes shielded storage receptacles for receiving and storing the probes when the probes are not in use. A reference standard is associated with each of the storage receptacles so that the stability of the radiation detector can be verified when the probes are positioned in the storage receptacles.

The first probe, more particularly, generates a signal that indicates moisture content of the test material. The first probe has a neutron radiation source that emits fast neutrons into the test material. A thermal neutron detector mounted in the first probe detects the thermal neutrons that have been moderated by neutron moderating elements present in the test material and generates a signal based on the thermal neutron count. The thermal neutron detector may, for example, be a $^3$He tube.

The second probe generates a signal that indicates the composition of the test material. The second probe includes a low energy gamma radiation source for emitting gamma radiation into the test material. A gamma radiation detector that is shielded from the gamma radiation source detects backscattered gamma radiation from the test material and generates a signal based on the count. The gamma radiation detector may, for example, be an x-ray proportional counter.

The present invention is particularly applicable for measuring the physical properties of fresh, unhardened concrete mix. A sample container is filled with fresh concrete and the probes are positioned in measuring contact with the concrete by removing the probes from storage receptacles provided in the instrument housing and inserting them one at a time into an elongate access tube that is centrally located in the sample container and is surrounded by the concrete. A moisture probe is inserted into the access tube in the sample container and neutrons are directed into the test material from a fast neutron source located in the probe. The thermal neutrons scattered from the material are detected and counted and a signal is generated that corresponds to the count. From this count, the moisture content of the cement mix can be determined.

Then a cement composition probe is inserted into the access tube, and gamma radiation is directed into the test material from a gamma radiation source located in the probe. The gamma radiation that is back-scattered by the test sample is detected and counted and a signal based thereon is generated which corresponds to the cement content of the sample. The water to cement ratio is calculated and displayed and the ultimate strength of the concrete is determined and displayed based on the calculated water to cement ratio.

BRIEF DESCRIPTION OF THE DRAWINGS

Some of the features and advantages of the invention have been stated. Other advantages will become apparent as the description of the invention proceeds, taken in conjunction with the accompanying drawings, in which.

DESCRIPTION OF THE PREFERRED EMBODIMENT

The present invention will now be described more fully with reference to the accompanying drawings, which illustrate particular embodiments of the apparatus. In the preferred embodiment, the present invention is a portable instrument for determining the moisture and cement content of a sample of a fresh, unhardened concrete mix and for determining and displaying the strength of the concrete mix to the user of the instrument.

Figure 1:
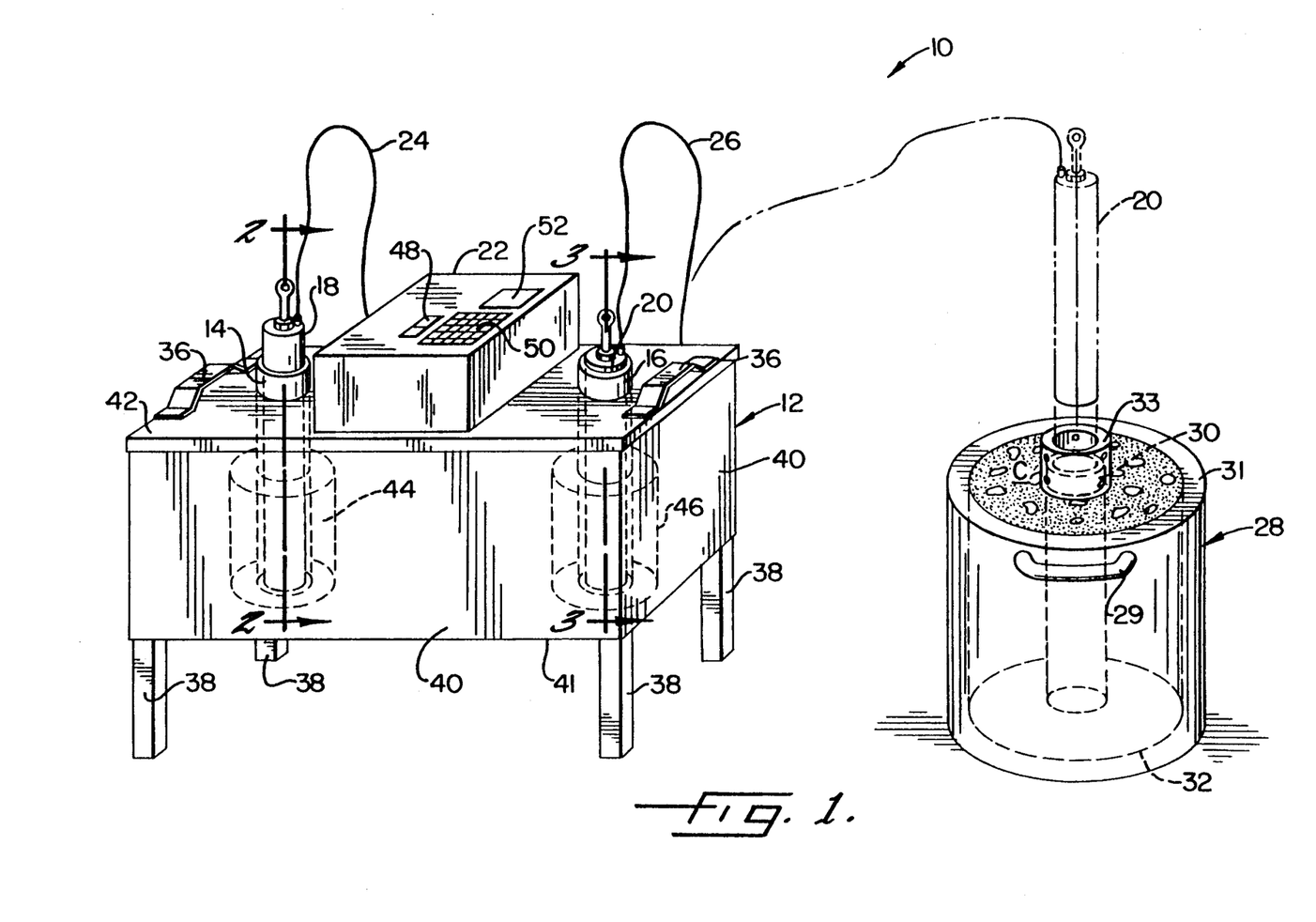
FIG. 1 is a perspective view of a preferred embodiment of the apparatus of the present invention.

An apparatus is generally identified in FIG. 1 by the numeral 10. An instrument housing is shown at 12 and includes receptacles 14 and 16 for a cement probe 18 and a moisture probe 20, respectively. The probes are shown in a storage position located in their respective receptacles. Probes 18 and 20 are connected to an electronic circuit 22 by means of electrical cables 24 and 26, respectively. The water to cement ratio can be empirically correlated with compressive strength for particular concrete mixes, and the probes 18 and 20 are used lo obtain the moisture and cement content measurements, which the electronic circuit 22 converts to a value for strength, as is explained below.

Moisture probe 20 is also shown in FIG. 1 in broken lines, having been removed from receptacle 16 and positioned for insertion into a sample container 28. Sample container 28 has a cylindrical outer wall 31 and a bottom plate 32. An access tube 30 is mounted on the bottom plate 32 and is centrally located in sample container 28. As illustrated in FIG. 1, sample container 28 is filled with fresh, unhardened concrete c.

Sample container 28 has handles 29 to provide for portability. The sample container is of a sturdy construction, capable of withstanding repeated rodding. In rodding, the operator will thrust a steel rod in a vertically downward motion through the concrete in the sample container and will also hit the sides of the container with a rawhide or rubber mallet. Rodding assures that the concrete sample completely fills the container and thus provides a sample of concrete of uniform density without air pockets. Preferably, the sample container 28 should be made of stainless steel or aluminum and should be approximately 12 to 14 inches in diameter and about 11 to 13 inches high. For the volumes of concrete that will fill such containers, the sample container 28 and handles 29 should be capable of supporting at least 150 pounds.

Access tube 30 in sample container 28 is essentially transparent to radiation and may comprise conventional materials, such as Schedule 40 PVC pipe that is connected to the bottom plate 32. The access tube 30 should be sized to extend beyond the top of the sample container and should be preferably equipped with an indexing device 33 that is capable of fixing the cement probe 18 at several (e.g. four) levels in a repeatable fashion. Access tube 30 and bottom plate 32 should be removable from sample container 28 and should be capable of being completely cleaned after each use.

Instrument housing 12 is sized so as to be portable by one person and includes carrying handles 36, as well as retractable legs 38 so that the housing may be elevated at least about six inches above the surface upon which the housing and probes are placed, such as the tail gate of a pickup truck or other such location at a construction site. Elevating the instrument reduces interference from the underlying surface with the measurements. The instrument housing 12 also includes sides 40, a bottom 41, and a top 42 for enclosing the internal components that are described in more detail hereinbelow.

An electronics unit 22 is mounted to the top 42 of the instrument housing 12 and is shown having an on-off switch 48 for controlling power to the electronics unit and a keypad 50 to enable the user of the instrument or other individual to control the function of the electronics unit. The keypad suitably is a conventional membrane that is made to be waterproof, dust proof and able to withstand five years of use in an outside environment. Preferably, the keypad 50 will have an easily replaceable plastic cover that can provide tactile feedback to the operator for accurate input of data. The electronics unit 22 also includes a display 52, which is preferably a liquid crystal display having large characters to improve clarity of menus and messages. The display 52 should be interactive to allow for built-in testing. Electronics unit 22 also includes (FIG. 4) a processor 54 having a memory 56 and an interface board 58 for interfacing of the processor 54 with the probes 18 and 20. These components are described in greater detail herein below with respect to FIG. 4.

Electronics unit 22 is normally attached to the instrument housing 12 and contains all of the electronics necessary for providing computations, power distribution, making the radiation counts, and providing a user interface. The unit is small, and may be approximately 8 inches deep, 4 inches high, and about 6-7 inches wide. In the embodiment shown, the electronics unit 22 is capable of being separated from instrument housing 12, being electrically connected thereto by a cord (not shown).

Figure 2:
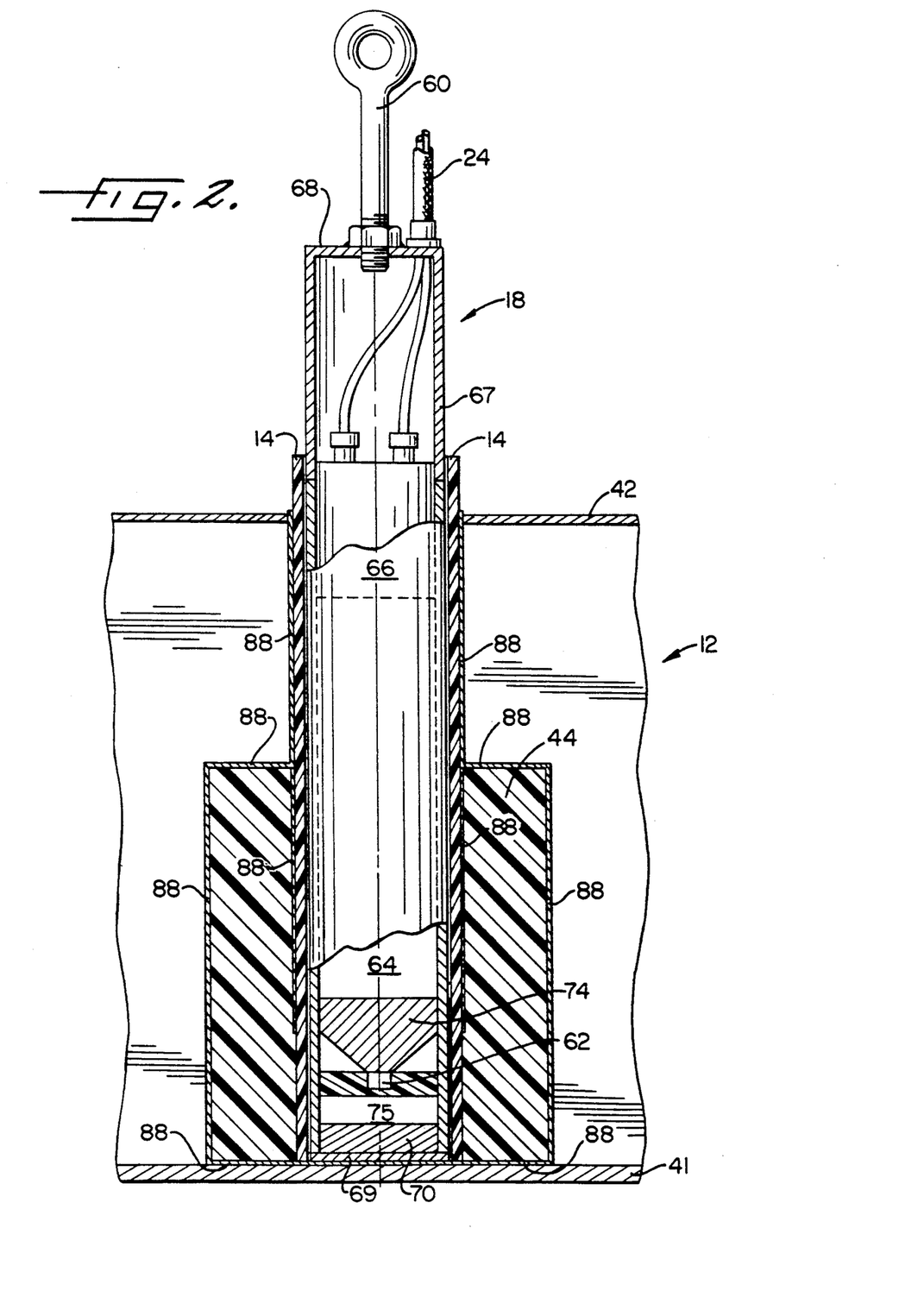
FIG. 2 is a longitudinal section of a portion of the apparatus that has been taken along the line 2—2 of FIG. 1.
Figure 4:
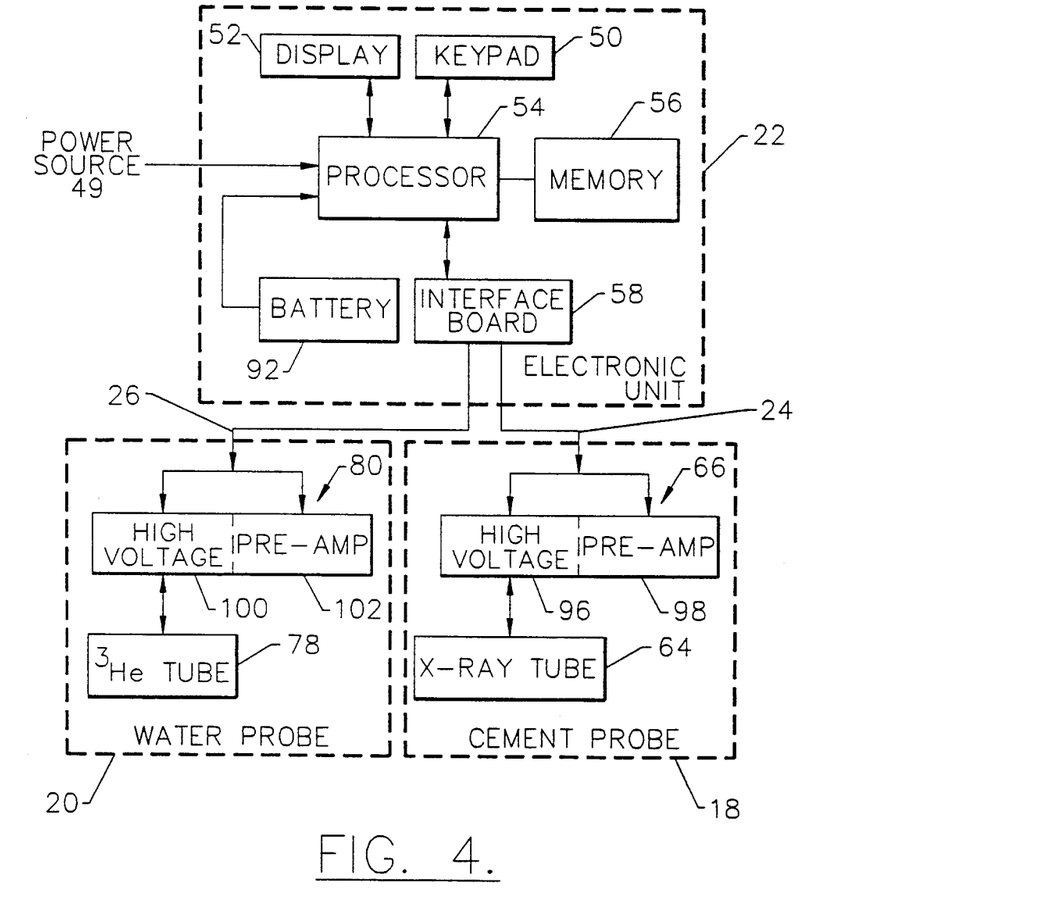
FIG. 4 is a schematic diagram of the electronic components of the apparatus.

FIG. 2 illustrates a longitudinal section through a portion of the instrument of FIG. 1 containing the cement probe 18 and taken along line 2—2 Of FIG. 1. As shown, the cement content probe 18 is of a generally cylindrical configuration and contains a handle 60 at one end and a gamma radiation source 62 near the opposite end thereof. A detector 64 is spaced from the gamma source for detecting gamma radiation that is backscattered by the concrete sample. An electronics module 66 at the opposite end of the cement probe 18 from the gamma radiation source 62 supplies power for driving the detector 64 and for providing a signal based on the count of backscattered gamma radiation through cable 24 to electronics unit 22 (FIG. 4). Gamma source 62, detector 64 and electronics module 66 are housed within a cylindrical probe body 67 having end caps 68 and 69. Probe body 67 preferably is formed of a thin-walled aluminum sleeve.

Lead radiation shields 70 and 74 are provided within the housing. Lower lead shield 70 is positioned adjacent the end cap 76 of the lower cylindrical probe body 68. Lower lead shield 70 is spaced from gamma radiation source 62 so as to provide an air gap 75. Upper lead shield 74 is interposed between the gamma radiation source 62 and detector 64. Upper lead shield 74 is conically shaped so that only gamma radiation that has been backscattered by the source will be counted by the detector 64. The shield prevents the detector from being saturated with photons that go directly into the detector without scattering in the concrete. The gamma radiation source 62 is preferably a 10 mCi $^{241}$Am point source, which emits gamma rays with an energy of 60 keV. Detector 64 is preferably an x-ray proportional gamma radiation counter or equivalent.

The cement probe is able to measure cement content because of photoelectric absorption of gamma radiation by calcium, which is a major component of Portland cement. The higher the atomic number of a particular atom, the higher the probability of photoelectric absorption at low photon energies. Most of the elemental constituents of a typical concrete mix have atomic numbers of 14 or lower, and so the contribution of these elements to photoelectric absorption is limited. However, calcium, which is a major component of cement, has an atomic number of 20. Therefore, as the cement content of a concrete mix increases, the calcium content also increases and the number of photons that are photoelectrically absorbed increases. The correlation for a specific concrete mix and probe count is linear, so the probe can be accurately calibrated for the mix. Such calibration techniques are within the skill of the ordinary artisan.

Electronics module 66 for the cement probe 18 should be capable of receiving a low voltage power from interface board 58 (FIG. 4) and converting it to a high voltage, approximately 1,900 VDC, for driving the x-ray tube, which is detector 64. Additionally, the pulses received by the electronics module 66 from x-ray tube 64 will be separated from the 1,900 VDC, buffered, and amplified before transmission to interface board 58. The pulses received from electronics unit 66 should be around 5 mV.

Figure 3:
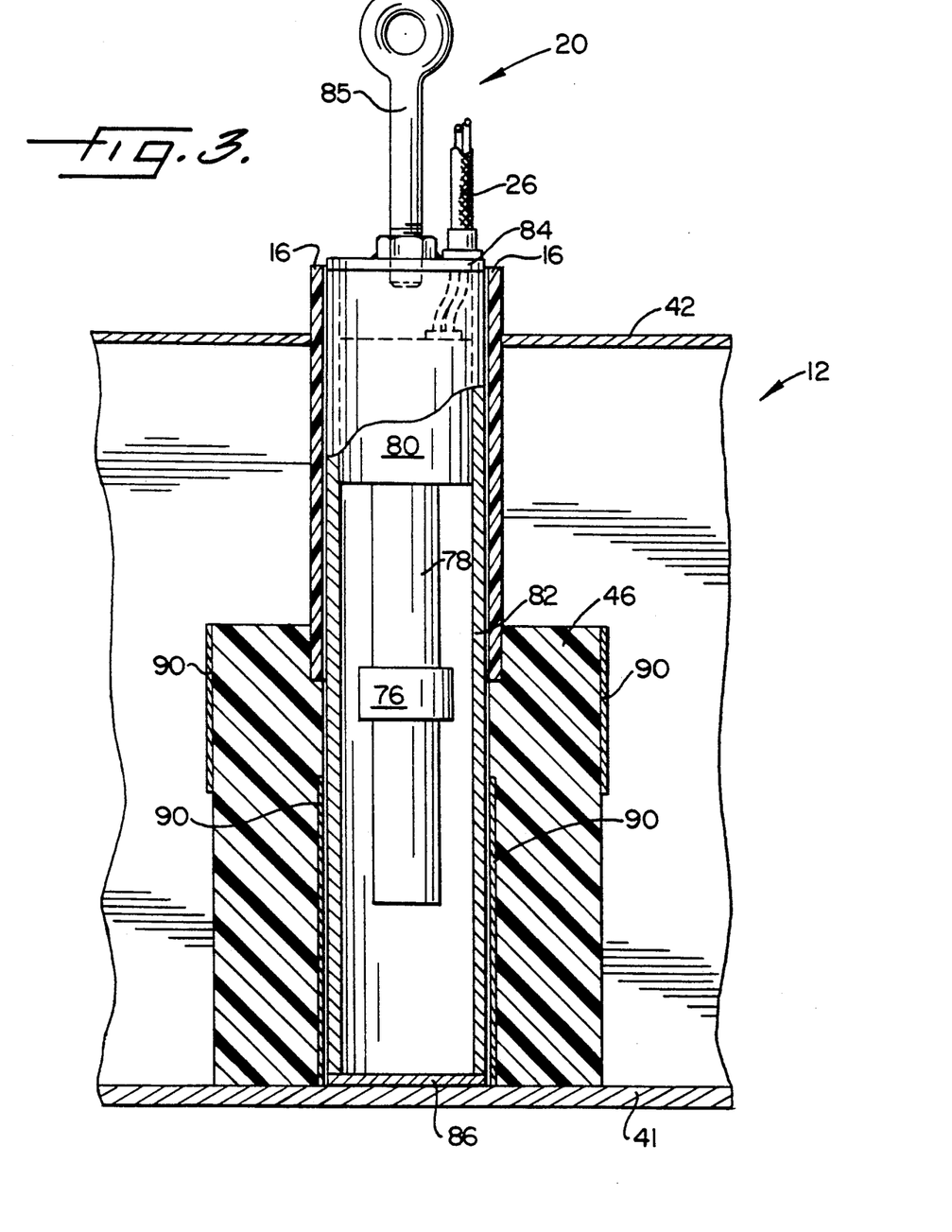
FIG. 3 is a longitudinal section of a portion of the apparatus that has been taken along the line 3—3 of FIG. 1.

FIG. 3 illustrates a longitudinal section through a portion of the instrument of FIG. 1 containing the moisture probe 20 and taken along line 3—3 of FIG. 1. Moisture probe 20 comprises a neutron source 76, a thermal neutron detector 78, and an electronics module 80. Fast neutrons emitted by the source 76 are thermalized through multiple collisions with atoms in the surrounding medium. By thermalized, it is meant that the neutrons are reduced in kinetic energy to the point where they are equally likely to gain energy through a collision as to lose energy. Some atoms, such as hydrogen, have a greater ability to thermalize fast neutrons than others. Therefore, the water component of concrete is most likely to thermalize fast neutrons. The correlation for a specific moisture content and probe count is linear, so the probe can be accurately calibrated for the water content of the mix.

Electronics module 80 converts the thermal neutron count to an electronic signal that is sent through cable 26 to the interface board 58 (FIG. 4) of the electronics unit 22. The neutron source 76, the thermal neutron detector 78, and the electronics module 80 are all housed in a cylindrical probe body 82 that serves as an outer shield. Probe body 82 preferably is made of aluminum and includes aluminum end caps 84 and 86 that seal the cylindrical probe body 82. Cable 26 is connected to the electronics module 80 through end cap 84. A handle for the probe is shown at 85.

Neutron source 76 preferably comprises a 10 mCi Am:Be annular source. Thermal neutron detector 78 is preferably a $^3$He tube upon which is centered neutron source 76. Electronics module 80 is interposed between the $^3$He neutron detection tube 78 and the end cap 84 at the top of the moisture probe 20. Electronics module 80 should be capable of receiving a low voltage power from interface board 58 (FIG. 4) and converting it to high voltage of approximately 900 VDC for driving the $^3$He tube. Electronics module so receives pulses from the tube 78 and separates and buffers the pulses for transmission to the interface board 58.

An important aspect of the present invention is the shielded storage receptacles 14 (FIG. 2) and 16 (FIG. 3) and the corresponding reference standards 44 and 46, respectively, that are provided for verifying the stability and accuracy of the radiation detectors 64 and 78, respectively, in the cement and moisture probes 18 and 20, respectively. The storage receptacles 14, 16 provide a convenient place to store the probes when not in use. The reference standard 44 for the cement probe 18 is an annular solid block of polyethylene which surrounds receptacle 14. Receptacle 14, which is essentially transparent to radiation and is preferably formed of PVC pipe, is inserted into polyethylene block 44. The polyethylene block 44 is surrounded on the top, sides, and bottom with lead foil shielding 88. The upper portion of the receptacle 14 that fits within the polyethylene block 44 is also wrapped in lead foil 88. Additionally, the portion of the receptacle 14 that extends immediately above polyethylene block 44 is lined with lead foil 88.

As shown in FIG. 3, reference standard 46 for moisture probe 20 is also an annular polyethylene block. The receptacle 16 is a PVC tube which is fitted into and extends upwardly from the annular polyethylene block. Lead foil shielding 90 is provided around the upper outer diameter of the polyethylene block 46 and the lower inside diameter of block 46.

FIG. 4 schematically illustrates the electronics that are used in connection with the present invention. Electronics unit 22 includes keypad 50, display 52, processor 54, a memory 56, an interface board 58, and a battery 92. Processor 54 may be connected to a power source 49. Also shown in FIG. 4 are the electronics for the cement probe 18 and the moisture probe 20 and their interconnection to the interface board 58 of electronics unit 22 through electrical cable connections 24 and 26, respectively.

The electronics unit 22 performs all of the computations, control input, and user interface functions. Electronics unit 22 provides a low voltage power to the probes 18 and 20 and receives analog pulses from the probe. Electronics unit 22 interfaces with the user via display 52 and keypad 50. Electronics unit 22 can be powered through internal battery 92 or through an external power source 49 such as a charger or an automobile cigarette lighter.

Processor 54 contains the central processing unit and all of the associated digital hardware, including ROM, RAM, non-volatile RAM, and a real time clock. Processor 54 is conventional, and its functions could easily be divided among various processor boards. Processor 54 controls probes and counts the digital pulses from interface board 58. Interface board 58 converts the pulses to raw counts and provides these results to processor 54. Processor 54 also provides interface to the keypad 50, display 52, and optional ports through which the electronic units may communicate. Processor 54 also controls the charging circuit for battery 92 and power distribution from the power sources 92 and 49.

Memory 56 preferably should have a sufficient battery-backed RAM for 50 total counts from both the water and cement measurements and 15 calibrations, including offset calibrations. Preferably, the battery-backing circuit will not be integral to the chip.

Interface board 58 provides the interface between the central processing unit of processor 54 and the probes 18 and 20. The interface board 58 should be capable of providing a low voltage power to one or both probes simultaneously based on the control signals from the processor 54. The interface board 58 should also be capable of receiving pre-amplified signals from both probes simultaneously, amplifying the signals, and converting the resulting pulses into digital pulses. The resulting two digital signals are then sent to the processor 54 where the calculations are performed.

Display 52 preferably consists of a suitably large liquid crystal diode such as a 20×4 LDC. Large character space will improve the clarity of menus and messages for use in the field. Preferably the display 52 will be interactive to allow for built-in testing. Buffers should be considered for improving processing speed, if necessary.

Also shown in FIG. 4, electronics module 66 of cement probe 18 includes a voltage converter 96 and a preamplifier amplifier 98. Cement probe 18 should be capable of receiving a low voltage power from interface board 58 and converting the low voltage power to a high voltage for driving the gamma radiation detector, x-ray tube 64, through voltage converter 96. Preamplifier 98 is provided to buffer the pulses before transmission to the interface board.

Similarly, electronics module 80 of moisture probe 20 includes a voltage converter 100 and a pre-amplifier 102. Moisture probe 20 receives low voltage power from interface board 58 and converts it to high voltage in voltage converter 100. Pulses received from neutron detector 78 are buffered and amplified prior to transmission to interface board 58 in preamplifier 102.

Cables 24 and 26 provide electrical signals between electronics unit 22 and cement probe 18 and moisture probe 20, respectively. Preferably, these cables are either coaxial cables or multiconductor cables with locking connectors at the end connecting to the electronics unit. Because the instrument will be used out of doors in a construction environment, the cable should be dust-proof and water-proof.

Figure 5A:
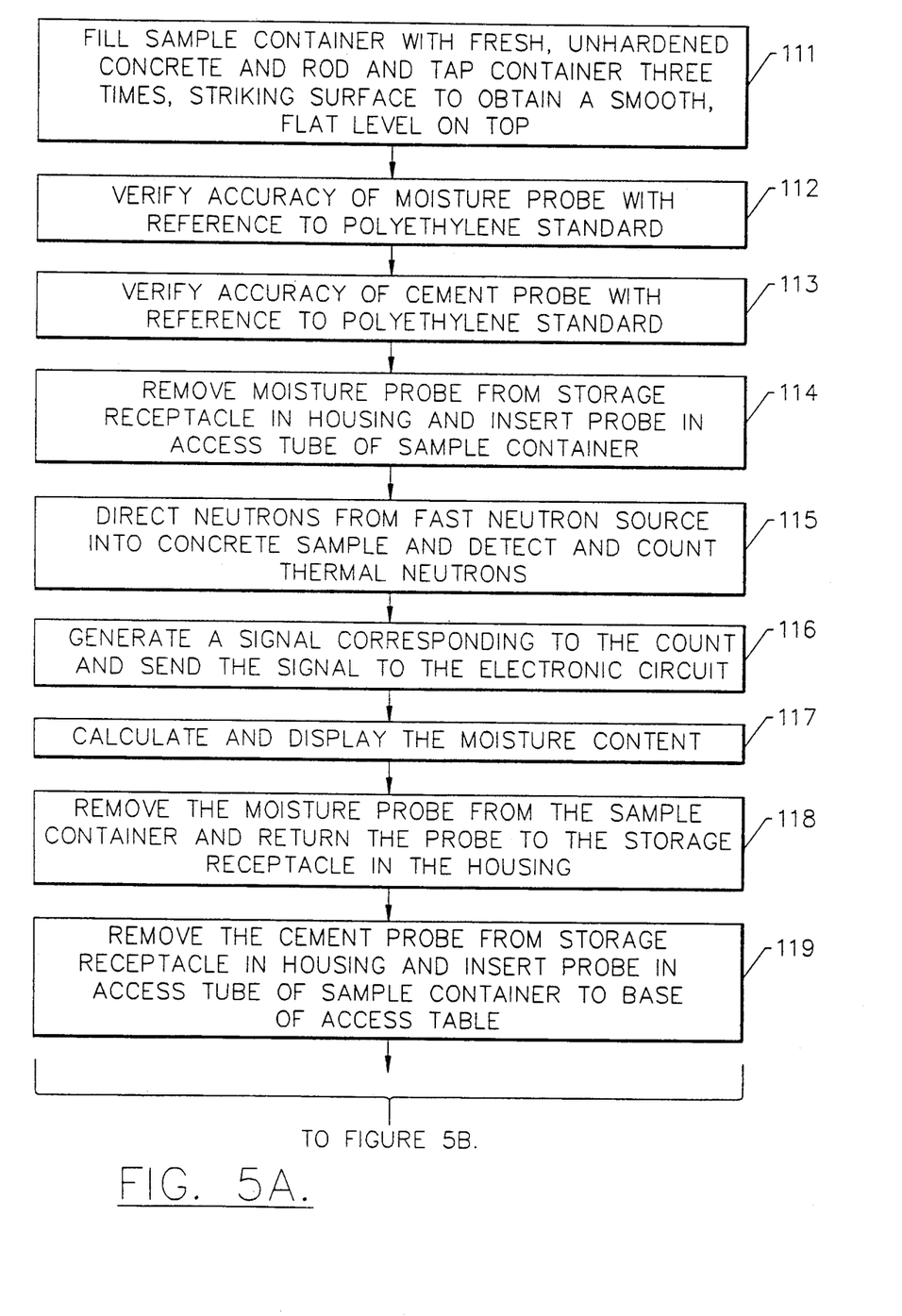
FIGS. 5A and 5B are a flow diagram depicting the steps performed in the practice of the present invention.
Figure 5B:
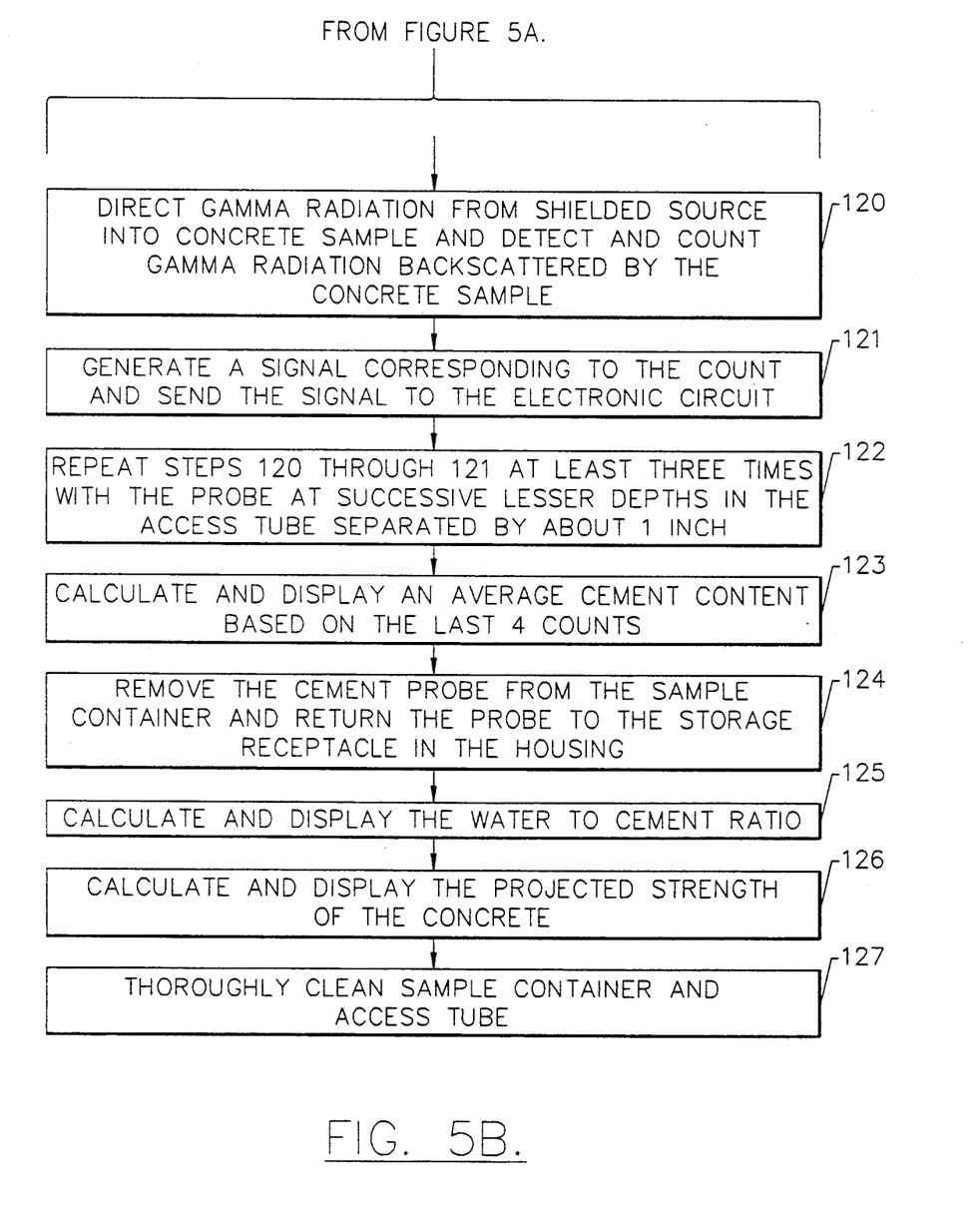

FIGS. 5A and 5B illustrate the operational aspects of the present invention and shows the various steps that the operator will take to obtain a measurement of the strength of fresh, unhardened concrete. As shown in step 111, the operator first fills the sample container 28 with fresh, unhardened concrete and then rods and taps the container at least three times while filling the container. The container should be rodded and tapped after it is ⅓ full, when it is ⅔ full, and when filled. After filling the container and completing the rodding and tapping operation, the operator strikes the surface to obtain a smooth, flat level surface on the top of the sample. Then, as shown in step 112, the operator will verify the accuracy of the moisture probe 20 with reference to polyethylene reference standard 46. In step number 113, the operator verifies the accuracy of the cement probe 18 with reference to polyethylene reference standard 44. These verifications are performed while the probes are inserted into their respective standards.

The correlations between cement content and the count obtained and between the water content and the count obtained can be empirically determined, and may be fitted to a linear or second order equation so that functions expressing these relationships may be stored in memory 56. Calibration curves for several concrete mixes may be stored in memory and recalled as needed. Also stored in memory 56 is the information to calculate the water-to-cement ratio in fresh concrete and to correlate this ratio with the ultimate strength of hardened concrete.

Typically, the calibration curves for the probes previously will have been generated in a laboratory setting based upon the concrete mixes that are expected in the field. For calibration of the cement content probe, a concrete mix is prepared, which is sometimes referred to as the "target mix," that is identical to that expected in the field. Measurements are taken in at least four samples of the target mix, the water and cement content of which are precisely known. Two additional concrete mixes are prepared, one of lower cement content than the target mix, and one of higher cement content than the target mix. The water content of these mixes is identical to that of the target mix. Measurements are taken of at least four samples of these mixes. A linear calibration curve is prepared based upon the measurements, in which the cement content is the independent variable. The slope and intercept of this curve are stored in memory 56.

The moisture probe is calibrated in a similar manner, only the cement content is kept constant in the mixes. Measurements are taken of a target mix having the expected water content of the field mix. Additional mixes are prepared, one with a higher water content and one with a lower water content to generate the slope and intercept for the calibration curve.

After filling the sample container and calibrating the probes, as shown in step 114, the operator removes the moisture probe from the storage receptacle in housing 12 and inserts it into access tube 30 of sample container 28. As shown in step 115, neutrons are directed from the fast neutron source 76 into concrete sample c. Some of these neutrons undergo multiple scatters until they either escape or are thermalized within the sample. A cloud of thermalized neutrons develops around the detector tube, and some are counted by the probe.

As shown in step 116, electronics module 80 generates a signal corresponding to the thermal neutron count and sends this signal to interface board 58 of electronic unit 22 in the form of pulses. The signal is amplified and provided to processor 54 for performing calculations to determine the moisture content of the cement. In step number 117, the processor 54 calculates the moisture content, which is displayed to the user by display 52. The count obtained is plugged into the function that has been stored for the correlation between moisture content probe count.

After the moisture content has been displayed, the user or operator, according to step 118, removes the moisture probe from the sample container and returns it to the storage receptacle provided in the instrument housing.

According to step 119, the operator then removes the cement probe from its storage receptacle in housing 12 and inserts it into the access tube 30 of sample container 28 to take the first cement measurement.

In accordance with step 120, gamma radiation is directed from the shielded source into the concrete sample. Some of the radiation undergoes multiple scatters until absorbed, and some scatters into the x-ray proportional counter, where the backscattered radiation is counted. Lead shielding prevents the detector from being saturated by photons that go directly into the detector without scattering into the concrete.

In accordance with step 121, electronics module 66 generates a signal corresponding to the count obtained in detector 64 and amplifies and sends this signal to the electronics unit 22. Steps 120 and 121 are preferably repeated at least three times (step 122) with the probe at successively lesser depths of about 1 inch to obtain additional counts. These counts are plugged into the function that has been stored for the relationship between cement content and probe count.

In accordance with step 123, the processor calculates and displays through the display an average cement content based upon the at least four counts that have been obtained. The operator then removes the cement probe from the sample container and returns it to the storage receptacle in the housing in accordance with step 124. Processor 54 calculates and displays through display 52 the water-to-cement ratio in accordance with step 125 and then, in accordance with step 126, processor 54 calculates and displays the projected strength of the concrete based on this ratio and stored functions relating this ratio to ultimate compressive strength. Finally, in accordance with step 127, the operator thoroughly cleans the sample container, access tube, and bottom plate in preparation for the next sample.

The instrument of the present invention is designed to be transportable by one person in a carrying case. The instrument is capable of being operated in an external environment, and it is contemplated that it will normally be used at construction sites on the tailgate of a pickup truck. The instrument of the present invention is capable of operating over an ambient temperature range of from −10° C. to 65° C. and at a humidity of up to 100%. Direct sunlight and heavy dust, including cement dust, is contemplated. The instrument is designed to withstand pressure water sprays and wet concrete splatter.

The foregoing description is to be considered illustrative rather than restrictive of the invention. This invention can be used in other contexts for measuring the physical properties of materials generally and is applicable to calculate and display at least one physical characteristic property of a test material from measurements taken with two probes. Therefore, it should be understood that the specific embodiment described herein is an illustration of how the present invention may be practiced. Those modifications that come within the meaning and range of equivalence of the claims are to be included in the foregoing description.

What is claimed is:

1. An instrument for measuring physical characteristics of a test material, comprising:

an instrument housing;

first and second movable probes associated with said housing, each being adapted to be individually positioned in measuring contact with a sample of the test material for obtaining a measurement therefrom, said first movable probe including means for obtaining a measurement of a first physical property of the test material, and said second movable probe including means for obtaining a measurement of a second physical property of the test material different from said first physical property;

an electronic circuit operatively connected to said first and second probes and including means for receiving from said probes respective first and second signals indicative of the measurements of said first and second physical properties, and means for determining from said signals a value for at least one physical characteristic of the test material; and a display device carried by said housing and being operatively connected to said electronic circuit for displaying to the user said value.

2. An instrument according to claim 1 wherein said first movable probe includes means for generating a signal indicative of the moisture content of the test material and said second movable probe includes means for generating a signal indicative of the composition of the test material.

3. An instrument according to claim 1 wherein said means for determining a value comprises means for determining from said first and second signals, which are indicative of first and second physical properties of the material, a value for a third physical property of the material different from said first and second physical properties.

4. An instrument according to claim 3 wherein the test material is fresh, unhardened concrete mix, and said first movable probe includes means for generating a signal indicative of the moisture content of the concrete mix and said second movable probe includes means for generating a signal indicative of the cement content of the concrete mix, and wherein said means for determining a value comprises means for determining from said moisture content and said cement content a value for the ultimate strength of the hardened concrete.

5. An instrument according to claim 1 wherein said first and second probes each comprise a low activity radiation source and a radiation detector, and wherein said instrument housing includes first and second shielded storage receptacles for receiving and storing the respective first and second probes when the probes are not in use.

6. An instrument according to claim 5 additionally including a reference standard associated with each of said first and second storage receptacles to permit verification of the accuracy of said radiation detectors in the respective probes when said probes are positioned in the storage receptacles.

7. An instrument according to claim 5 wherein said first probe includes a low activity neutron radiation source for emitting fast neutrons into the test material, and a thermal neutron detector mounted in predetermined spaced relationship to said neutron source for detecting thermal neutrons that have been moderated by neutron moderating elements present in the test material.

8. An instrument according to claim 7 wherein said first probe is of an elongate cylindrical configuration, said thermal neutron detector comprises a $^3$He tube located in said cylinder, and said neutron source is centered on the $^3$He tube.

9. An instrument according to claim 5 wherein said second probe includes a low activity gamma radiation source for emitting gamma radiation into the test material, and a gamma radiation detector mounted in predetermined spaced relationship to said gamma radiation source for gamma radiation that has been backscattered from the test material.

10. An instrument according to claim 9 wherein said second probe is of an elongate cylindrical configuration, said gamma radiation source is located adjacent one end of the elongate cylindrical probe, said gamma radiation detector includes an X-ray proportional counter located adjacent the opposite end of the elongate cylindrical probe, and said second probe further comprises shielding positioned between said source and said counter and between said source and said opposite end of said probe.

11. An instrument for measuring physical characteristics of a test material, comprising:
    an instrument housing;
    first and second movable probes associated with said housing, each being adapted to be individually positioned in measuring contact with a sample of the test material for obtaining a measurement therefrom,
    said first movable probe including a low activity neutron radiation source for emitting fast neutrons into the test material, and a thermal neutron detector mounted in predetermined spaced relationship to said neutron source for detecting thermal neutrons that have been moderated by hydrogen present in the test material and for thereby generating a signal that is indicative of the moisture content of the test material, and
    said second movable probe including a low activity gamma radiation source for emitting gamma radiation into the test material, and a gamma radiation detector mounted in predetermined spaced relationship to said gamma radiation source for detecting gamma radiation that has been backscattered from the test material for thereby generating a signal that is indicative of the composition of the test material;
    an electronic circuit operatively connected to said first and second probes and including means for receiving from said probes respective first and second signals indicative of the moisture content and the composition of the test material, and means for determining from said signals a value for at least one physical characteristic of the test material; and
    a display device carried by said housing and being operatively connected to said electronic circuit for displaying to the user said value.

12. An instrument according to claim 11 wherein said electronic circuit includes means for independently displaying via said display device, a value for the moisture content and the composition of the test material.

13. An instrument according to claim 11 wherein said instrument housing comprises first and second shielded storage receptacles for receiving and storing the respective first and second probes when the probes are not in use.

14. An instrument according to claim 13 additionally including a reference standard associated with each of said first and second storage receptacles to permit verification of the accuracy of said radiation detectors in the respective probes when said probes are positioned in the storage receptacles.

15. An instrument for measuring the projected ultimate strength of hardened concrete by physical measurements taken on a test sample of the concrete mix in the unhardened plastic state; said instrument comprising:
    a sample container including a pan adapted for receiving a test sample of concrete mix in the unhardened plastic state, and an elongate access tube centrally mounted in the pan so as to be substantially surrounded by concrete mix when the pan is filled with concrete mix;
    an instrument housing;
    first and second elongate movable probes associated with said housing, each being adapted to be individually positioned in the elongate access tube of said sample container in measuring contact with a sample of the concrete mix for obtaining a measurement therefrom,
    said first movable probe including a low activity neutron radiation source for emitting fast neutrons into the test material, and a thermal neutron detector mounted in predetermined spaced relationship to said neutron source for detecting thermal neutrons that have been moderated by hydrogen present in the test material and for thereby generating a signal which is indicative of the moisture content of the concrete mix, and
    said second movable probe including a low activity gamma radiation source for emitting gamma radiation into the concrete mix, and a gamma radiation detector mounted in predetermined spaced relationship to said gamma radiation source for detecting gamma radiation that has been backscattered from the concrete mix for thereby generating a signal which is indicative of the cement content of the concrete mix;
    an electronic circuit operatively connected to said first and second probes and including means for receiving from said probes respective first and second signals indicative of the moisture content and the cement content of the concrete mix, and means for determining from said signals a value for the projected ultimate strength of the concrete after hardening and curing; and
    a display device carried by said housing and being operatively connected to said electronic circuit for displaying to the user said value.

16. An instrument according to claim 15 wherein said electronic circuit includes means for storing a correlation between the projected ultimate strength of concrete and the water to cement ratio of the unhardened concrete mix, and means applying the measured moisture content and cement content values of a test sample to said stored correlation to determine therefrom the projected strength of a sample of concrete mix.

17. An instrument according to claim 15 wherein said instrument housing comprises first and second shielded storage receptacles for receiving and storing the respective first and second probes when the probes are not in use.

18. An instrument according to claim 17 additionally including a reference standard associated with each of said first and second storage receptacles to permit verification of the accuracy of said radiation detectors in the respective probes when said probes are positioned in the storage receptacles.

19. A method for measuring the physical characteristics of a test material, comprising:
  a) positioning a first movable probe in measuring contact with a sample of the test material;
  b) obtaining a measurement from the first probe and generating a signal from the measurement that is indicative of a first physical property of the test material;
  c) sending the signal generated in accordance with step (b) to an electronic circuit;
  d) removing the first probe from measuring contact with the test material;
  e) positioning a second movable probe in measuring contact with the sample of the test material;
  f) obtaining a measurement from the second probe and generating a signal from the measurement that is indicative of a second physical property of the test material;
  g) sending the signal generated in accordance with step (f) to the electronic circuit;
  h) determining in the electronic circuit a value for at least one physical characteristic of the test material from the signals sent by the probes in steps (c) and (g); and
  i) displaying in a display device the value determined in accordance with step (h).

20. The method of claim 19 wherein the step of obtaining a measurement from the first probe comprises directing neutrons from a fast neutron source located in said probe into the test material and detecting and counting thermal neutrons that have been moderated by neutron moderating elements present in the test material.

21. The method of claim 19 wherein the step of obtaining a measurement from the second probe comprises directing gamma radiation from a gamma radiation source located in said probe into the test material and detecting and counting the backscattered gamma radiation.

22. The method of claim 19 including the step of filling a sample container with the test material and wherein the steps (a) and (e) of positioning the probes in measuring contact with the test material comprise inserting the probe in an elongate access tube that is centrally located in the sample container and is substantially surrounded by the test material.

23. The method of claim 19 including the additional step of verifying the stability of each of the probes by placing the probes in close proximity with reference standards.

24. The method of claim 19 including the additional steps of displaying values for the first and second physical properties in the display device.

25. The method of claim 19 including the additional steps of determining a value for a third physical property from the signals generated in accordance with steps (b) and (f) and displaying the third value.

26. A method for measuring the physical characteristics of a test material, comprising:
  a) positioning a first movable probe in measuring contact with a sample of the test material;
  b) directing neutrons from a fast neutron source located in said probe into the test material and detecting and counting thermalized neutrons to generate a signal that is indicative of a first physical property of the test material;
  c) sending the signal generated in accordance with step (b) to an electronic circuit;
  d) removing the first probe from measuring contact with the test material;
  e) positioning a second movable probe in measuring contact with the sample of the test material;
  f) directing gamma radiation from a gamma radiation source located in said second probe into the test material and detecting and counting the backscattered gamma radiation to generate a signal that is indicative of a second physical property of the test material;
  g) sending the signal generated in accordance with step (f) to the electronic circuit;
  h) determining in the electronic circuit a value for at least one physical characteristic of the test material from the signals sent by the probes in steps (c) and (g); and
  i) displaying in a display device the value determined in accordance with step (h).

27. The method of claim 26 including the additional step of verifying the accuracy of each of the probes by placing the probes into close proximity with reference standards.

28. The method of claim 26 including the additional steps of displaying values for the first and second physical properties in the display device.

29. The method of claim 26 including the additional steps of determining a value for a third physical property from the signals generated in accordance with steps (b) and (f) and displaying the third value.

30. A method for measuring the ultimate strength of concrete from the moisture content and composition of fresh unhardened concrete mix, comprising:
  a) positioning a first movable probe in measuring contact with a sample of the concrete mix;
  b) obtaining a measurement from the first probe and generating a signal from the measurement that is indicative of the moisture content of the concrete mix;
  c) sending the signal generated in accordance with step (b) to an electronic circuit;
  d) removing the first probe from measuring contact with the concrete mix;
  e) positioning a second movable probe in measuring contact with the sample of the concrete mix;
  f) obtaining a measurement from the second probe and generating a signal from the measurement that is indicative of the cement content of the concrete mix;
  g) sending the signal generated in accordance with step (f) to the electronic circuit;
  h) determining in the electronic circuit a value for the ultimate strength of the hardened concrete from the signals sent by the probes in steps (c) and (g); and
  i) displaying in a display device the value for the ultimate strength of the hardened concrete determined in accordance with step (h).

31. The method of claim 30 wherein the step of obtaining a moisture content measurement from the first probe comprises directing neutrons from a fast neutron source located in said first probe into the sample of concrete mix and detecting and counting thermalized neutrons.

32. The method of claim 30 wherein the step of obtaining a cement content measurement from the second probe comprises directing gamma radiation from a gamma radiation source located in said second probe into the sample of concrete mix and detecting and counting the backscattered gamma radiation.

33. The method of claim 30 including the step of filling a sample container with concrete mix and wherein the steps (a) and (e) of positioning the probes in measuring contact with the sample of concrete mix comprise removing the probe from a storage receptacle in the housing and inserting the probe in an elongate access tube that is centrally located in a sample container and is substantially surrounded by concrete mix.

34. The method of claim 30 including the additional steps of storing a correlation between the projected ultimate strength of concrete and the water to cement ratio of unhardened concrete mix, determining the water to cement ratio for the sample of concrete mix from the signals generated in accordance with steps (b) and (f), respectively, and applying the ratio to the stored correlation to determine the ultimate strength of the hardened concrete.

35. The method of claim 30 including the additional steps of displaying the water and cement content values in the display device.

* * * * *